United States Patent [19]

Nuyken et al.

[11] Patent Number: 5,037,961

[45] Date of Patent: Aug. 6, 1991

[54] POLYMERIZABLE ARYLDIAZOSULPHONATES DIAZOSULPHONATE GROUPS AND ETHYLENICALLY UNSATURATED GROUPS BOUND TO AROMATIC RADICALS

[76] Inventors: Oskar Nuyken, Ignaz-Guenther-Strasse 12, D 8000 Muenchen 81; Thomas Knepper, Talstrasse 11, D 6581 Schauren; Brigitte Voit, Friedrich von Schiller-Strasse 3 a, D 8580 Bayreuth; Stephen D. Pask, Bayer Aktiengesellschaft, P.O. Box 100140, D 4047 Dormagen, all of Fed. Rep. of Germany

[21] Appl. No.: 336,877

[22] Filed: Apr. 12, 1989

[30] Foreign Application Priority Data

Apr. 27, 1988 [DE] Fed. Rep. of Germany ....... 3814164

[51] Int. Cl.$^5$ ..................... C07C 245/02; C08F 12/00
[52] U.S. Cl. .................... 534/558; 534/565; 534/573; 526/219; 526/240; 526/241; 526/287
[58] Field of Search ................ 534/558, 563; 514/150

[56] References Cited

U.S. PATENT DOCUMENTS

| | | | |
|---|---|---|---|
| 2,154,509 | 4/1939 | Kern | 534/558 |
| 3,086,057 | 4/1963 | Sarkar | 534/558 X |
| 3,132,159 | 5/1964 | Hartzler | 534/558 |
| 4,515,940 | 5/1985 | Berthold | 534/556 X |
| 4,663,308 | 5/1987 | Saffran et al. | 534/523 P X |

FOREIGN PATENT DOCUMENTS 0877402 9/1961 United Kingdom .

OTHER PUBLICATIONS

Ida et al., J. Pharm. Soc. Japan, vol. 89, pp. 524 to 530 (1969).
Martynoff, Chemical Abstracts, vol. 49, 8876d (1955).
Chemical Abstracts, 83:61601g (1975).
R. Puttner, "Aryldiazosulphonates" in Methoden der Organischen Chemie, pp. 570 et seq. (1965).
J. DeJonge, R. Dijkstra, Rec. Trav. Chim. 75, 290 (1965).
H. Jonker, Th. P. G. W. Thiyssens, L. K. H. van Beek, Rec. Trav. Chim. 87, 997 (1968).
Th. Knepper, O. Nuyken, B. Voit, Makromol. Chem. 190, 1015 (1989).
O. Nuyken, B. Voit, Makromol. Chem. 190, 1325 (1989).
A. Stasko, O. Nuyken, B. Voit, S. Biskupic, Tetr. Lett., vol. 31, No. 40, 5737 (1990).

*Primary Examiner*—Mary C. Lee
*Assistant Examiner*—Fiona T. Powers

[57] ABSTRACT

Aryldiazosulphonates having polymerizable ethylenically unsaturated groups are excellent starting materials for water-soluble homopolymers and copolymers, which can be converted to water-soluble polymers by irradiation. Thus, the polymers can be utilized for the preparation of aqueous coating compositions.

4 Claims, No Drawings

POLYMERIZABLE ARYLDIAZOSULPHONATES DIAZOSULPHONATE GROUPS AND ETHYLENICALLY UNSATURATED GROUPS BOUND TO AROMATIC RADICALS

The invention relates to aryldiazosulphonates containing polymerizable groups, to a process for their preparation, to the use of the novel aryldiazosulphonates for the preparation of polymers, and to polymers containing recurring units with aryldiazosulphonate groups.

"Aryldiazosulphonates" in the context of the invention are compounds having at least one sulphonate group (per molecule) directly bound to the diazo group. The conventional azo dyes are (apart from missing polymerizable groups) therefore—since diazo groups and sulphonate groups are each separated by some kind of structural units—not aryldiazosulphonates in the context of the invention.

". . . sulphonate" in the context of the invention denotes —SO$_3$M in which M represents hydrogen, NH$_4$, NR'$_4$ (in which R'=CH$_3$, C$_2$H$_5$, C$_3$H$_7$ or C$_4$H$_9$), or an equivalent of Al, Zn or Cu, but preferably alkali metal or an equivalent of an alkaline earth metal.

For the first time, we have now synthesized aryldiazosulphonates having ethylenically unsaturated groups polymerizable by free radicals. These novel aryldiazosulphonates can be polymerized to give homopolymers and copolymers, of which in particular the water-soluble polymers are of paramount interest. Water-soluble polymers containing recurring units with aryldiazosulphonate groups can be converted into water-insoluble products by irradiation; it may be assumed that the irradiation cleaves or eliminates the diazo group. It is possible that first the corresponding diazonium cations are formed, which in the presence of water and with elimination of nitrogen are converted to the corresponding phenol. The water-solubility of the polymers can be reduced by irradiation to such an extent that the difference in water-solubility of irradiated and non-irradiated areas can be exploited for useful industrial purposes; the non-irradiated areas can be, for example, washed out with water, thus leading to the formation of images, e.g. on hydrophilic supports such as aluminum to form a printing plate.

The invention therefore relates to aryldiazosulphonates having
(i) at least 1, preferably 1 to 4, aromatic C$_6$-C$_{10}$-radical(s),
(ii) at least 1, preferably 1 to 3, diazosulphonate group(s) bound to an aromatic radical and
(iii) at least 1, preferably 1 or 2, ethylenically unsaturated group(s) polymerizable by free radicals and bound to an aromatic C$_6$-C$_{10}$-radical Preferred unsaturated groups (iii) contain 1 to 2 polymerizable C=C bonds per group.

Preferred aromatic radicals (i) comprise phenylene and naphthalene, preferred unsaturated groups (iii) conforming to the formula $$X-R_n- \qquad (I)$$

in which
X denotes —C=CH$_2$, —CCH$_3$=CH$_2$, —CH=CHCH$_3$, —CCN=CH$_2$, —CH=CHCN, —CCl=CH$_2$, —CH=CHCl, —OCOCH=CH$_2$, 
—OCOCH=CHCH$_3$, —OCOCCH$_3$=CH$_2$, —COOCCH$_3$=CH$_2$,
—COOCH=CHCH$_3$, —CH=CH—CH=CH$_2$, —O—CH=CH$_2$,
—O—CCH$_3$=CH$_2$ or —O—CH=CH—CH$_3$, preferably —CH=CH$_2$,
—CCH$_3$=CH$_2$, —OCOCCH$_3$=CH$_2$ or —O-COCH=CH$_2$, R denotes C$_1$-C$_{10}$-alkylene, C$_6$-C$_{18}$-arylene, C$_1$-C$_{10}$-alkyleneoxy, C$_6$-C$_{18}$-aryleneoxy, C$_1$-C$_{10}$-alkylenecarboxyamino, C$_1$-C$_{10}$-alkylenecarbamoyl, C$_7$-C$_{19}$-arylenecarbamoyl, C$_1$-C$_{10}$-alkyleneamino and C$_6$-C$_{18}$-aryleneamino and n denotes zero or 1.

Particularly preferred aryldiazosulphonates are those whose diazosulphonate groups (ii) are bound to the same aromatic radicals (i) as the polymerizable groups (iii).

The preferred aryldiazosulphonates are those of the formula

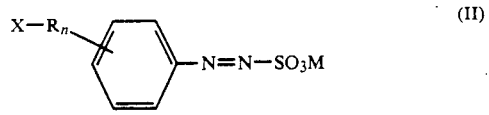

in which M has the above mentioned meaning and preferably stands for potassium or sodium. In the most preferred aryldiazosulphonates, X denotes —CH=CH$_2$ and n denotes zero.

The aryldiazosulphonates according to the invention can be prepared in analogy to the procedures from "Methoden der Organischen Chemie" (Methods of Organic Chemistry) (Houben-Weyl), Vol. 10/3, Georg Thieme Verlag, Stuttgart 1965, or from German Offenlegungsschrift No. 3,125,104 from arylamines containing polymerizable groups by diazotization and subsequent reaction with sulphite, preferably alkali metal or alkaline earth metal sulphite. The reaction is preferably carried out at temperatures of from −20 to 120, in particular of from 0 to 50, most preferably from 0° to 30° C., and at a pH of 4 to 13, in particular 4 to 5 or 8 to 10.

The novel aryldiazosulphonates can be polymerised to form homopolymers and copolymers with aryldiazosulphonate groups in the chain. Alternatively such polymers can be formed by first polymerising the arylamines containing polymerisable groups and then converting the amine groups into diazosulphonate groups by diazotation and reaction with sulphite as referred to hereinbefore.

Monomers which are polymerizable by free radicals and are suitable for the copolymerization using the aryldiazosulphonate according to the invention are preferably those having 1 to 2 ethylenically unsaturated polymerizable groups and 2 to 12 carbon atoms, such as, for example, styrene, methyl methacrylate, acrylonitrile, methyl acrylate, ethyl acrylate, acrylamide, methacrylamide, acrylic acid, methylacrylic acid, ethylacrylic acid, butadiene and isoprene and also mixtures of two or more of these monomers. Styrene, acrylonitrile, butadiene and methyl methacrylate are preferred comonomers.

Not only the homopolymers but also the copolymers can be prepared in solution or in an emulsion by methods known per se. The molecular weights of the homopolymers and copolymers may be from 10,000 to 1,000,000, preferably from 10,000 to 100,000, measured by gel permeation chromatography on polystyrene columns using tetrahydrofuran as the eluant and compared to polymethyl methacrylate as the standard; pore sizes of the standards: $10^6$, $10^4$, $10^3$ and 500 Ångström.

Copolymers obtainable from the novel aryldiazosulphonates can contain 1 to 99, preferably 10 to 50, mol % of units containing aryldiazosulphonate groups and 99 to 1, preferably 90 to 50, mol % of copolymerized units of one or more other monomers.

The homopolymers and copolymers according to the present invention can be characterized by containing recurring units with aryldiazosulphonate groups, the said arydiazosulphonate groups having
(i) at least 1, preferably 1 to 4, aromatic $C_6$–$C_{10}$ radical(s)
(ii) at least 1, preferably 1 to 3 diazosulphonate group(s) bound to an aromatic radical.

Preferred aromatic groups are phenylene and naphthylene.

If water-soluble copolymers are desired, the required minimum amount of the necessary aryldiazosulphonate groups depends on the polarity of the monomers used and on the molecular weight of the desired copolymer. In general, copolymers prepared from

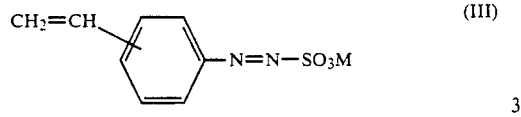

(III)

and styrene become water-soluble above 25 mol % of III and copolymers prepared from III and methyl methacrylate become water-soluble above 15 mol % of III.

Particularly preferred water-soluble copolymers consist of more than 90, in particular 100, % by weight of units with aryldiazosulphonate groups, styrene and/or methyl methacrylate.

"Water-soluble" in the context of the invention means that at a concentration of at least 35 g of polymer per liter of water at 45° C. not more than 1 g of polymer is insoluble.

The water-soluble homopolymers and copolymers can be processed without difficulty from aqueous solution to give films, which can be dried preferably at an elevated temperature and, if necessary, under reduced pressure. The coatings from the polymer solution can be self-supporting or applied to a support.

The water-soluble polymers with recurring units containing aryldiazosulphate groups can be reacted to give water-insoluble products by means of high-energy radiation such as, for example, UV light, X-rays and electron rays. The reaction rate depends on the wavelength, light intensity and, in some cases, on the distance of the radiation source from the polymer. In many cases, a mercury/xenon high-pressure lamp should be suitable. A film having a layer thickness of 0.1 mm and consisting of a copolymer prepared from 80 mol % of methyl methacrylate and 20 mol % of III becomes water-insoluble, for example, after 10 minutes of irradiation using a mercury/xenon high-pressure lamp (132 W, distance 30 cm). Optimum results can be obtained by irradiation with a wavelength corresponding to the absorption maximum of the polymer.

The polymers according to the invention can be used as binders for printing inks and decorative coating agents, as photoresists for printed circuits and for the preparation of electronic components, as coating on hydrophilic supports to form after image-wise exposure and wash-off development a printing master, etc.

In the following examples, percentages relate in each case to the weight.

EXAMPLES

Example 1

Synthesis of sodium 3-vinylphenyldiazosulphonate
Synthetic Route

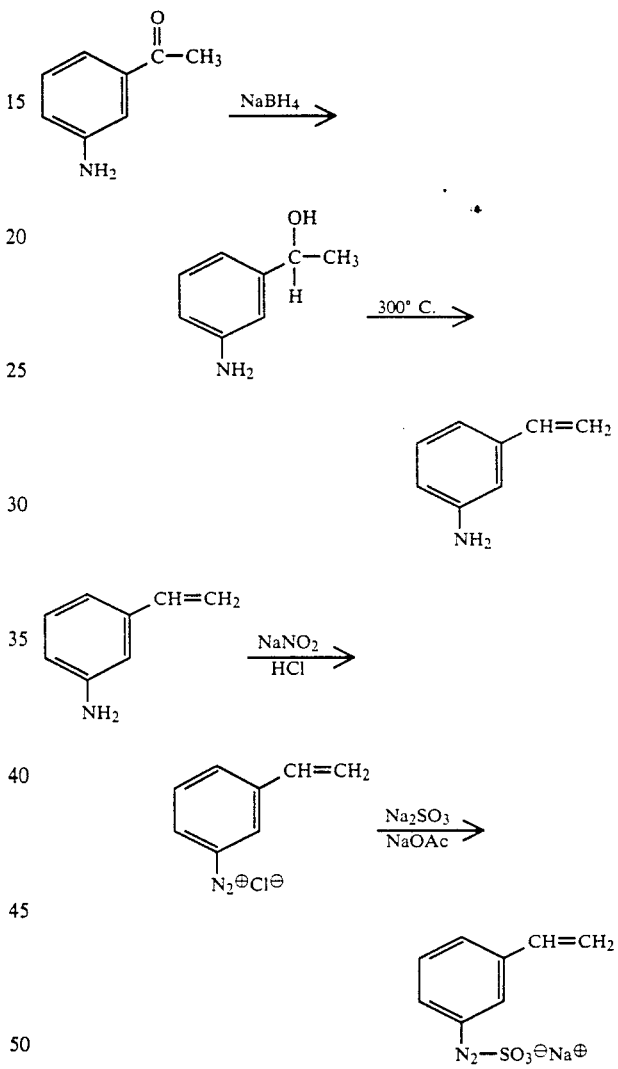

Procedure: 3-Aminostyrene 135 g (1 mol) of 3-aminoacetophenone are suspended in 1,000 ml of isopropanol, and 19 g (0.5 mol) of sodium borohydride are slowly added. The reaction mixture is stirred at room temperature for 48 hours and then brought to a pH of 5 with concentrated hydrochloric acid, while cooling with ice. The salt which is precipitated is filtered off with suction, and the slightly reddish solution is concentrated on a rotary evaporator under a water pump vacuum. The desired 1-(3-aminophenyl)ethanol crystallizes overnight in the cold, is filtered off with suction and dried.

The alcohol is subsequently dehydrated at 300° C. by means of an aluminium oxide catalyst in a heated tube. The product is taken up in water and extracted from the aqueous phase by shaking with ether, the organic phase is dried over sodium sulphate and the solvent is evaporated.

Yield: 77.3 g.

Sodium 3-vinylphenyldiazosulphonate 12 g (0.1 mol) of 3-aminostyrene are cooled to −5° C. in 100 ml of 10% strength aqueous hydrochloric acid. A previously cooled solution of 6.9 g (0.1 mol) of sodium nitrite in 50 ml of water is slowly added dropwise to this solution. The reaction solution is stirred at 0° C. for another 30 minutes and then rapidly added to a cold solution at −5° C. of 25.2 g (0.2 mol) of Na$_2$SO$_3$ and 33 g (0.4 mol) of sodium acetate in 150 ml of water. Upon cooling with ice, the product precipitates and can be filtered off with suction. It is washed with a small amount of cold water and recrystallized from ethanol. This gives 11.7 of a yellow powder.

Example 2

Synthesis of the sodium salt of 3-diazosulphobenzyl methacrylate.

Synthetic route:

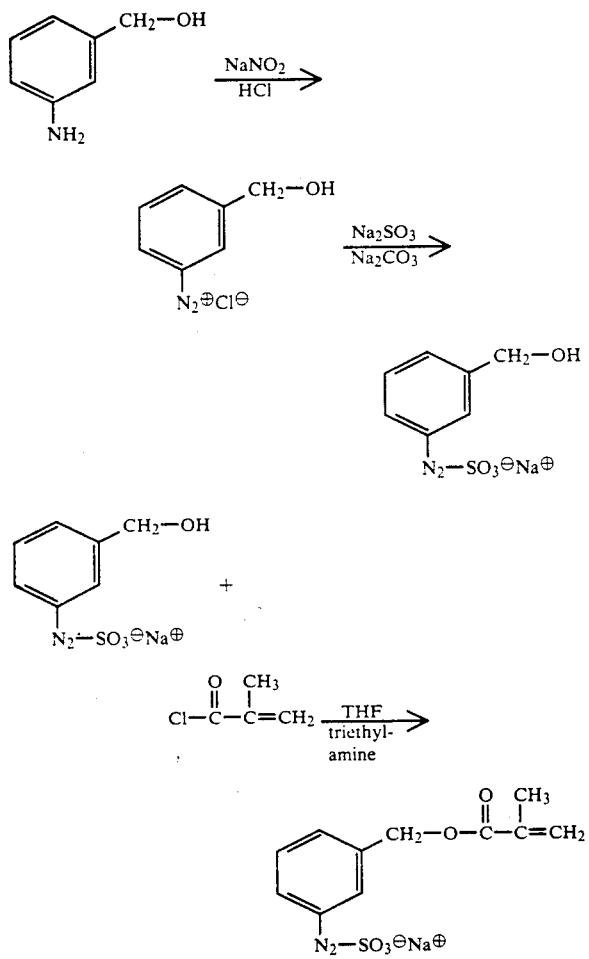

The aminobenzyl alcohol is diazotized analogously to 3-aminostyrene (Example 1) and reacted with sodium sulphite.

0.1 mol of the resulting sodium salt of 3-diazosulphobenzyl alcohol are dissolved in 500 ml of THF and cooled to −10° C. 0.12 mol of methacryloyl chloride are then added. 0.12 mol of triethylamine dissolved in 150 ml of THF are added dropwise to this mixture, and the resulting mixture is subsequently stirred for another 15 minutes at −10° C. The mixture is then warmed to room temperature and stirred for another hour. The product which precipitates is then filtered off with suction and recrystallized from ethanol.

Yield: 14.3 g

Working examples 3-5

Copolymers from 3-vinylphenyldiazosulphonate and methyl methacrylate (MMA) Reaction batch:

0.05 mol of methyl methacrylate+sodium vinylphenyldiazosulphonate
0.3 mmol of azoisobutyronitrile (=0.05 g) or
0.6 mmol of azoisobutyronitrile (=0.1 g)
50 ml of dioxane/water (ratio by volume 8:2), degassed.

The polymerization is carried out at 70° C. under an inert gas (N$_2$). Reaction vessel and reaction solution are freed from oxygen by purging with nitrogen. The solvent and the monomers are initially introduced. The polymerization is then initiated by the addition of the initiator. Depending on the azo content in the mixture, the reaction times are between 3 and 6 hours. The polymerization is stopped by ice cooling and addition of a small amount of hydroquinone. The solvent and unconverted MMA are evaporated on a rotary evaporator under a water pump vacuum, the resulting product is dissolved in dioxane/chloroform (ratio by volume 4:1) (>90 mol % of MMA) or in chloroform/methanol (ratio by volume 1:1) (<90 mol % of MMA) and precipitated by pouring this solution into a 10-fold excess, relative to the weight, of hexane; the copolymer is filtered off, washed with ice-cold water for a short time and dried in vacuo until the weight remains constant.

TABLE 1

| Example | MMA content of the monomer mixture (mol %) | Reaction time (hours) | Azo content in the polymer* (% by weight) | Molecular weight (GPC/THF) |
| --- | --- | --- | --- | --- |
| 3 | 90 | 3 | 7 | 20,000 |
| 4 | 85 | 4 | 10 | 16,000 |
| 5 | 80 | 6 | 12 | 11,500 |

*determined by UV absorption at 291 nm and the absorption coefficient for sodium 3-methylphenyldiazosulphonate.

The copolymer from Example 3 was soluble in methanol/water (1:1 parts by volume) and the copolymers from Examples 4 and 5 were water-soluble. The copolymers are dissolved in these solvents at 65° C. to give a 10% strength by weight solution; from these solutions, films having a dry film layer thickness of 0.1 mm are prepared on glass substrates. The films are dried at 80° C. in vacuo (0.1 torr) for 3 hours. After drying, the films are still soluble—as shown by control experiments—in the solvents mentioned. After irradiation using a mercury/xenon high-pressure lamp (132 watt, distance 20 cm), the films are insoluble in the solvents mentioned so that only non-irradiated areas could be washed out.

We claim:

1. Aryldiazosulphonate containing 1-4 aryls each with 6-10 carbon atoms and substituted by a total of 1-3 diazosulphonates and 1-2 substituents of the formula X—R$_n$—wherein X is —C=CH$_2$, —CCH$_3$=CH$_2$, —CH=CHCH$_3$, —CCN=CH$_2$, —CH=CHCN,
—CCl=CH$_2$, —CH=CHCl, —OCOCH=CH$_2$,
—OCOCH=CHCH$_3$, —OCOCCH$_3$=CH$_2$, —COOCCH$_3$=CH$_2$, —COOCH=CHCH$_3$, —CH=CH—CH=CH$_2$, —O—CH=CH$_2$,
—O—CCH$_3$=CH$_2$ or —O—CH=CH—CH$_3$, R is C$_1$-C$_{10}$-alkylene, C$_6$-C$_{18}$-arylene, C$_1$-C$_{10}$-alkyleneoxy, C$_6$-C$_{18}$-aryleneoxy, C$_1$-C$_{10}$-alkylenecarboxyamino, C$_1$-C$_{10}$-alkylenecarbamoyl, C$_7$-C$_{19}$-arylenecarbamoyl, C$_1$-C$_{10}$-alkyleneamino or C$_6$-C$_{18}$-aryleneamino, and n is 0 or 1.

2. Aryldiazosulphonate according to claim 1 wherein the aryl is phenylene or naphthylene.

3. Aryldiazosulphonate according to claim 1 wherein —R$_n$—X contains one or two polymerizable —C=C— bonds.

4. Aryldiazosulphonate of the formula

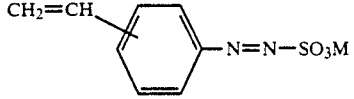

in which M stands for hydrogen, NH$_4$, NR'$_4$ (where R'=C$_1$-C$_4$-alkyl), alkali metal or one valence portion of an alkaline earth metal, Al, Ni, Zn, Cu.

* * * * *